(12) United States Patent
Lee et al.

(10) Patent No.: US 12,728,016 B2
(45) Date of Patent: Sep. 8, 2026

(54) TOTAL ANKLE REPLACEMENT INSTRUMENTS, ASSEMBLY, AND METHODS OF USE

(71) Applicant: Paragon 28, Inc., Englewood, CO (US)

(72) Inventors: Daniel J. Lee, Denver, CO (US); Joseph Dogué, Aurora, CO (US); Greg Marik, Germantown, TN (US); Spanky Raymond, Uniontown, OH (US)

(73) Assignee: Paragon 28, Inc., Englewood, CO (US)

( * ) Notice: Subject to any disclaimer, the term of this patent is extended or adjusted under 35 U.S.C. 154(b) by 906 days.

(21) Appl. No.: 18/154,946

(22) Filed: Jan. 16, 2023

(65) Prior Publication Data

US 2023/0210671 A1 Jul. 6, 2023

Related U.S. Application Data

(63) Continuation of application No. PCT/US2021/042022, filed on Jul. 16, 2021.

(60) Provisional application No. 62/705,801, filed on Jul. 16, 2020.

(51) Int. Cl.

*A61F 2/46* (2006.01)
*A61F 2/42* (2006.01)

(52) U.S. Cl.

CPC .......... *A61F 2/4606* (2013.01); *A61F 2/4202* (2013.01); *A61F 2/4637* (2013.01); *A61F 2002/4205* (2013.01); *A61F 2002/4207* (2013.01); *A61F 2002/4625* (2013.01); *A61F 2002/4627* (2013.01)

(58) Field of Classification Search

CPC ........ A61F 2/4202; A61F 2/46; A61F 2/4603; A61F 2/4606; A61F 2/4637; A61F 2002/4205; A61F 2002/4207; A61F 2002/4625; A61F 2002/4627

See application file for complete search history.

(56) References Cited

U.S. PATENT DOCUMENTS 4,100,626 A 7/1978 White
4,447,915 A 5/1984 Weber
(Continued)

FOREIGN PATENT DOCUMENTS

WO WO-2006099270 A2 * 9/2006 ........... A61F 2/4202
WO WO-2022016082 A1 * 1/2020 ........... A61F 2/4606
(Continued)

OTHER PUBLICATIONS

Extended European Search Report for European Application No. 21843261.5, Jul. 1, 2024, 7 pages.
(Continued)

*Primary Examiner* — Eric S Gibson
(74) *Attorney, Agent, or Firm* — Heslin Rothenberg Farley & Mesiti P.C.; Jacquelyn A. Graff, Esq.

(57) ABSTRACT

The present disclosure relates to an instrument. The instrument includes a handle coupled with a rod, and a body portion configured to receive the rod in a central portion thereof. The instrument also includes a coupling portion configured to releasably couple with one or more components of an implant. Actuation of the handle drives the rod to actuate a first implant component relative to a second implant component so as to position the first implant component adjacent the second implant component.

17 Claims, 8 Drawing Sheets

(56) References Cited

U.S. PATENT DOCUMENTS

| | | | | |
|---|---|---|---|---|
| 7,534,246 | B2 * | 5/2009 | Reiley | A61B 17/15 623/21.18 |
| 8,308,734 | B2 * | 11/2012 | Evans | A61F 2/4611 606/90 |
| 9,918,724 | B2 * | 3/2018 | Luna | A61F 2/4684 |
| 9,974,588 | B2 * | 5/2018 | Stemniski | A61B 17/15 |
| 11,311,302 | B2 * | 4/2022 | Luna | A61B 90/39 |
| 2006/0229730 | A1 * | 10/2006 | Railey | A61B 17/15 623/23.44 |
| 2014/0336658 | A1 * | 11/2014 | Luna | A61B 17/15 606/87 |
| 2015/0157467 | A1 * | 6/2015 | McGinley | A61B 17/1739 606/86 R |
| 2015/0257899 | A1 * | 9/2015 | Luna | A61F 2/4684 623/21.18 |
| 2017/0071753 | A1 | 3/2017 | Josse | |
| 2018/0344328 | A1 * | 12/2018 | McGinley | A61F 2/4606 |
| 2020/0113712 | A1 * | 4/2020 | Luna | A61B 17/1682 |
| 2021/0113222 | A1 * | 4/2021 | Khatibi | A61B 17/1775 |
| 2021/0298920 | A1 * | 9/2021 | Dalton | A61F 2/4657 |
| 2023/0210671 | A1 * | 7/2023 | Lee | A61F 2/4202 |

FOREIGN PATENT DOCUMENTS

| | | | | |
|---|---|---|---|---|
| WO | 2020124047 | | 6/2020 | |
| WO | WO-2020123307 | A1 * | 6/2020 | A61F 2/4684 |

OTHER PUBLICATIONS

International Search Report and Written Opinion of the International Searching Authority for PCT/US2021/042022, Nov. 2, 2021, 8 pages.

International Preliminary Report on Patentability for International Application No. PCT/US2021/042022 dated Jan. 17, 2023, 6 pages, International Bureau of WIPO.

* cited by examiner

TOTAL ANKLE REPLACEMENT INSTRUMENTS, ASSEMBLY, AND METHODS OF USE

CROSS-REFERENCE TO RELATED APPLICATIONS

This application is a continuation of PCT Application No. PCT/US2021/042022, filed Jul. 16, 2021, and entitled "Total Ankle Replacement Instruments, Assembly, and Methods of Use," which claims priority benefit under 35 U.S. C. § 119 (e) of U.S. Provisional Application No. 62/705,801, filed Jul. 16, 2020, entitled "Total Ankle Replacement Instruments, Assembly, and Methods of Use," which are incorporated herein by reference in their entireties.

FIELD

The present disclosure relates to soft tissue implant systems, instruments, and related methods. The present disclosure relates to podiatric and orthopedic implants and surgery related to repairs of soft tissue and/or bone. More specifically, but not exclusively, the present disclosure relates to instruments, implants, devices, systems, assemblies, and methods for joining soft tissue to soft tissue, soft tissue to bone, and bone to bone.

BACKGROUND OF THE INVENTION

Many currently available instruments for total ankle replacements do not allow for one or more components of a total ankle system to be quickly and consistently placed (and/or positioned, repositioned, or removed) by the user. Furthermore, currently available instruments

SUMMARY

The present disclosure is directed toward implants, devices and methods for use in maintaining, correcting and/or resurfacing joint surfaces.

A first aspect of the present disclosure is a system. The system includes an implant system having a tibial component, a talar component, and an intermediate component. The system also includes an instrument having a handle portion, a head portion with a releasable coupling mechanism that releasably couples with the tibial component of the implant system, and a body portion positioned between the handle portion and the head portion.

According to the first aspect of the present disclosure, the head portion is configured to releasably couple with the intermediate component.

According to the first aspect of the present disclosure, the tibial component and intermediate component are simultaneously releasably couplable with the head portion of the instrument such that the tibial component is positioned superiorly relative to the intermediate component.

According to the first aspect of the present disclosure, the handle portion includes a gripping portion and a threaded rod, wherein the threaded rod extends at least partially into and through the body portion of the implant.

According to the first aspect of the present disclosure, the body portion includes complimentary threading that receives at least a portion of the threaded rod.

According to the first aspect of the present disclosure, manipulation of the gripping portion actuates the threaded rod along a longitudinal axis of the instrument.

According to the first aspect of the present disclosure, actuation of the threaded rod along the longitudinal axis repositions the intermediate component relative to the tibial component in a proximal-distal direction.

A second aspect of the present disclosure is an instrument. The instrument includes a handle coupled with a rod, and a body portion configured to receive the rod in a central portion thereof. The instrument also includes a coupling portion configured to releasably couple with one or more components of an implant.

According to the second aspect of the present disclosure, actuation of the handle drives the rod to actuate a first implant component relative to a second implant component so as to position the first implant component adjacent the second implant component.

According to the second aspect of the present disclosure, the coupling portion includes a projection configured to engage at least a portion of the one or more components of the implant.

According to the second aspect of the present disclosure, the coupling portion includes an actuator configured to facilitate engagement with and the release of the one or more components of the implant via the projection.

According to the second aspect of the present disclosure, the first implant component is an insert for a total ankle replacement implant.

According to the second aspect of the present disclosure, the second implant component is a tibial tray for a total ankle replacement implant.

According to the second aspect of the present disclosure, the rod includes a first threading disposed along a length of the rod.

According to the second aspect of the present disclosure, the instrument includes a second threading disposed in the body, wherein the second threading is complimentary to and receives the first threading and the actuation of the handle causes translation of the rod through the body via the first and second threading.

According to the second aspect of the present disclosure, the first implant component is releasably couplable to the second implant component.

According to the second aspect of the present disclosure, the coupling portion is configured to releasably couple with the second implant component such that the second implant component remains in a fixed position while the first implant component is actuated.

According to the second aspect of the present disclosure, the coupling portion includes a catch and a notch.

According to the second aspect of the present disclosure, the second implant component includes a complimentary geometry to the catch and the notch such that the catch is received by a portion of the second implant component.

A third aspect of the present disclosure is a method of positioning implant components. The method includes selecting a desired size of a first implant component and a corresponding size of a second implant component, and releasably coupling the first implant component and the second implant component with a distal end of an insertion instrument, wherein the first implant component is arranged superiorly relative to the second implant component. The method also includes selectively repositioning the second implant component relative to the first implant component, positioning the first and second implant components relative to a tibia of a patient, and decoupling the first and second implant components from the insertion instrument.

BRIEF DESCRIPTION OF THE DRAWINGS

The accompanying drawings, which are incorporated in and constitute a part of the specification, illustrate embodiments of the inventions and together with the detailed description herein, serve to explain the principles of the inventions. It is emphasized that, in accordance with the standard practice in the industry, various features may or may not be drawn to scale. In fact, the dimensions of the various features may be arbitrarily increased or reduced for clarity of discussion. The drawings are only for purposes of illustrating embodiments of inventions of the disclosure and are not to be construed as limiting the inventions.

DETAILED DESCRIPTION

Figure 1:
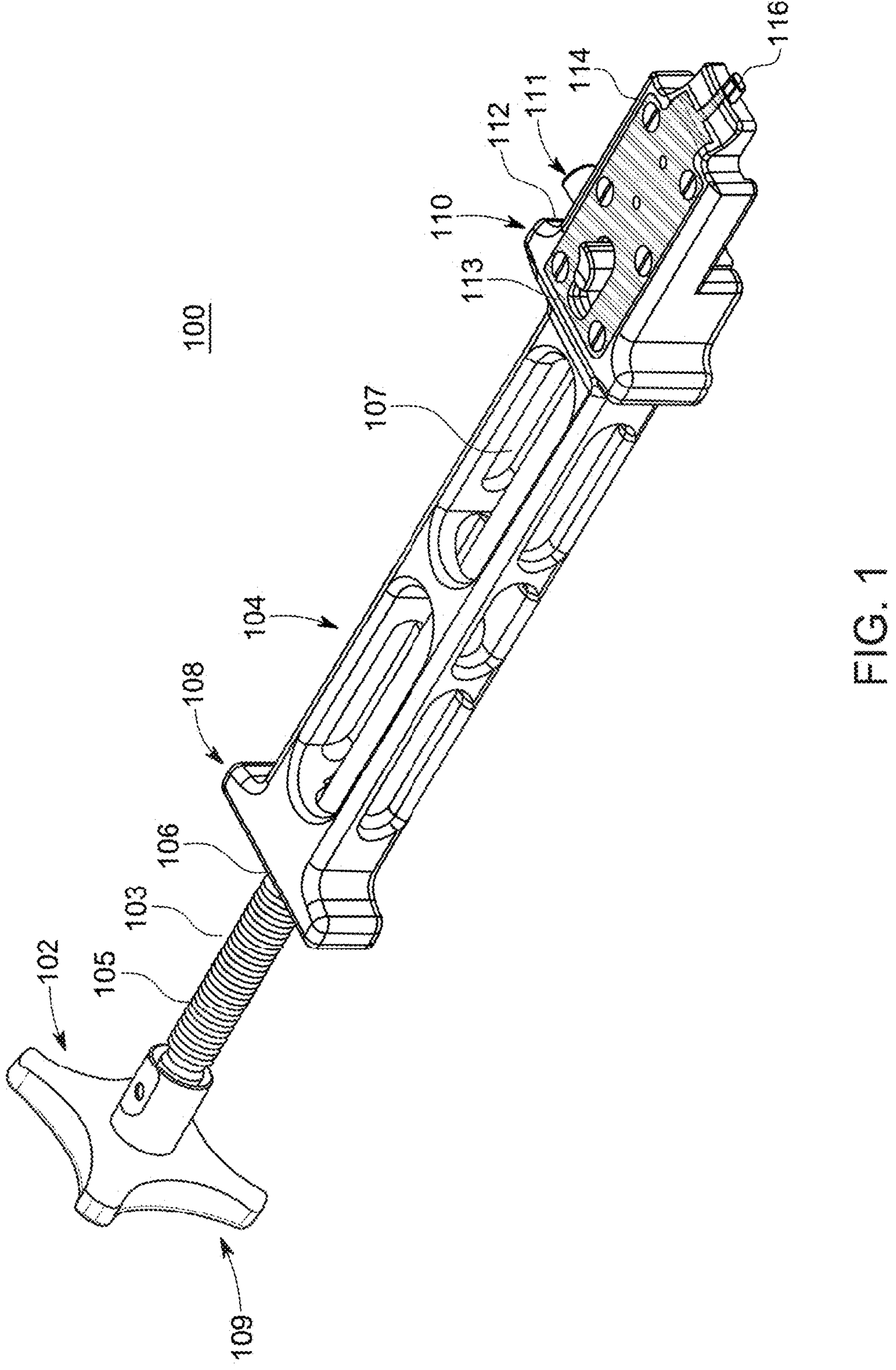
FIG. 1 is a side elevational perspective view of an exemplary instrument for facilitating the implantation of an implant system, in accordance with the present disclosure.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation, and methods are described herein with reference to use with the bones of the foot, the bones of the foot, ankle and lower leg may be used to describe the surfaces, positions, directions or orientations of the implants, devices, instrumentation and methods. Further, the implants, devices, instrumentation, and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation, and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation, and methods, and the aspects, components, features and the like thereof, described herein with respect to the right foot may be mirrored so that they likewise function with the left foot. Further, the implants, devices, instrumentation, and methods, and the aspects, components, features and the like thereof, disclosed herein are described with respect to the foot for brevity purposes, but it should be understood that the implants, devices, instrumentation, and methods may be used with other bones of the body having similar structures.

The instruments, implants, systems, assemblies, and related methods for maintaining, correcting, and/or resurfacing joint surfaces of the present disclosure may be similar to, such as include at least one feature or aspect of, the implants, systems, assemblies and related methods disclosed in International PCT Application No. PCT/US2019/29009, filed on Apr. 24, 2019, and entitled Implants and Methods of Use and Assembly; International PCT Application No. PCT/US2019/64741, filed on Dec. 12, 2019, and entitled Implant System and Methods of Use; International PCT Application No. PCT/US2019/66336, filed on Dec. 13, 2019, and entitled Patient Specific Instrumentation and Methods of Use; and/or International PCT Application No. PCT/US2019/66408, filed on Dec. 13, 2019, and entitled Joint Replacement Alignment Guides, System, and Methods of Use and Assembly; and/or International PCT Application No. PCT/US2019/66149 filed on Dec. 13, 2019, and entitled Alignment Instruments and Methods for Use in Total Ankle Replacement; and/or International PCT Application No. PCT/US2019/66393, filed on Dec. 13, 2019, entitled Joint Replacement Alignment Guides, Systems, and Methods of Use and Assembly; and/or U.S. Provisional Patent Application No. 62/898,615, filed on Sep. 11, 2019, entitled Resection Guides, Sweeping Reamers, and Methods for Use in Total Ankle Replacement; and/or International PCT Application No. PCT/US2019/66398, files on Dec. 13, 2019, entitled Distractors Having Attachable Paddles, Impaction Devices, and Methods for Use in Total Ankle Replacement; and/or International PCT Application No. PCT/US2019/65025, filed on Dec. 6, 2019, entitled Trial Insert Assembly;

and/or U.S. Provisional Patent Application No. 62/899,460 filed Sep. 12, 2019, entitled Total Ankle Replacement Surgical Method; and/or International PCT Application No. PCT/US2019/66404 filed on Dec. 13, 2019, entitled Instruments, Guides, and Related Methods for Total Ankle Replacement; which are hereby incorporated herein by reference in their entireties. Similarly, the instruments, implants, systems, assemblies, and related methods for maintaining, correcting, and/or resurfacing joint surfaces of the present disclosure may include one or more instrument (e.g., one or more insertion and/or implantation instruments) disclosed in International PCT Application No. PCT/US2019/29009, filed on Apr. 24, 2019, and entitled Implants and Methods of Use and Assembly; International PCT Application No. PCT/US2019/64741, filed on Dec. 12, 2019, and entitled Implant System and Methods of Use; International PCT Application No. PCT/US2019/66336, filed on Dec. 13, 2019, and entitled Patient Specific Instrumentation and Methods of Use; and/or International PCT Application No. PCT/US2019/66408, filed on Dec. 13, 2019, and entitled Joint Replacement Alignment Guides, System, and Methods of Use and Assembly; and/or International PCT Application No. PCT/US2019/66149 filed on Dec. 13, 2019, and entitled Alignment Instruments and Methods for Use in Total Ankle Replacement; and/or International PCT Application No. PCT/US2019/66393, filed on Dec. 13, 2019, entitled Joint Replacement Alignment Guides, Systems, and Methods of Use and Assembly; and/or U.S. Provisional Patent Application No. 62/898,615, filed on Sep. 11, 2019, entitled Resection Guides, Sweeping Reamers, and Methods for Use in Total Ankle Replacement; and/or International PCT Application No. PCT/US2019/66398, files on Dec. 13, 2019, entitled Distractors Having Attachable Paddles, Impaction Devices, and Methods for Use in Total Ankle Replacement; and/or International PCT Application No. PCT/US2019/65025, filed on Dec. 6, 2019, entitled Trial Insert Assembly; and/or U.S. Provisional Patent Application No. 62/899,460 filed Sep. 12, 2019, entitled Total Ankle Replacement Surgical Method; and/or International PCT Application No. PCT/US2019/66404 filed on Dec. 13, 2019, entitled Instruments, Guides, and Related Methods for Total Ankle Replacement; which are hereby incorporated herein by reference in their entireties.

Referring to the drawings, wherein like reference numerals are used to indicate like or analogous components throughout the several views, and with particular reference to FIGS. 1-6, there is illustrated an exemplary embodiment of an instrument 100 (e.g., inserter, insertion instrument, etc.) for positioning and/or repositioning a device, implant, or portion thereof adjacent one or more joint surfaces (e.g., between two joint surfaces, interfacing with one or more joint surfaces, etc.).

FIGS. 1-7 illustrate an exemplary instrument, shown as the inserter 100, for placing, positioning, or repositioning one or more components of a system used in total ankle replacement in accordance with the present disclosure. The inserter 100 is position and place a portion of a device, implant, and/or system used in a total ankle replacement procedure adjacent one or more joint surfaces of a patient.

Figure 2:
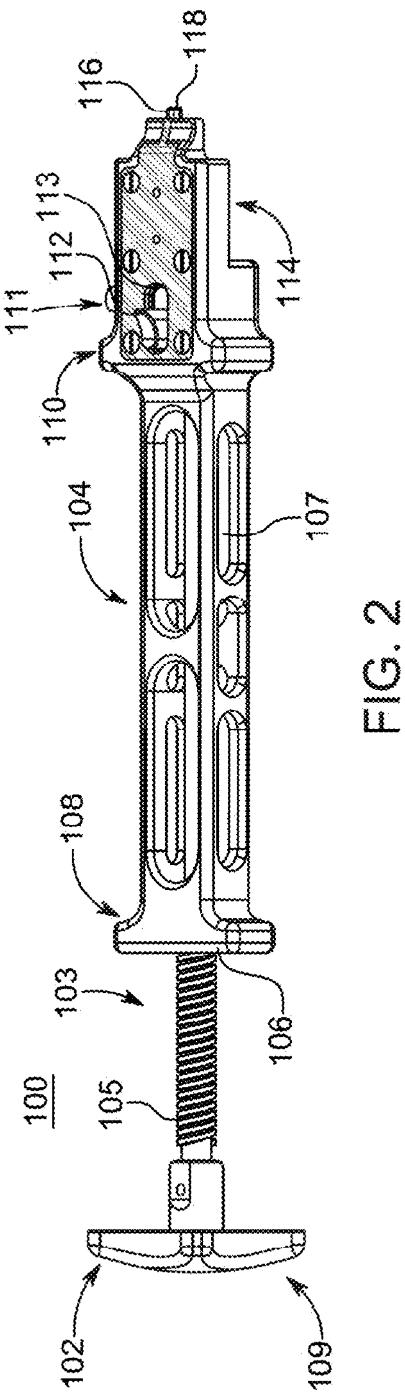
FIG. 2 is a side perspective view of the exemplary instrument of FIG. 1 for facilitating the implantation of an implant system, in accordance with the present disclosure.
Figure 3:
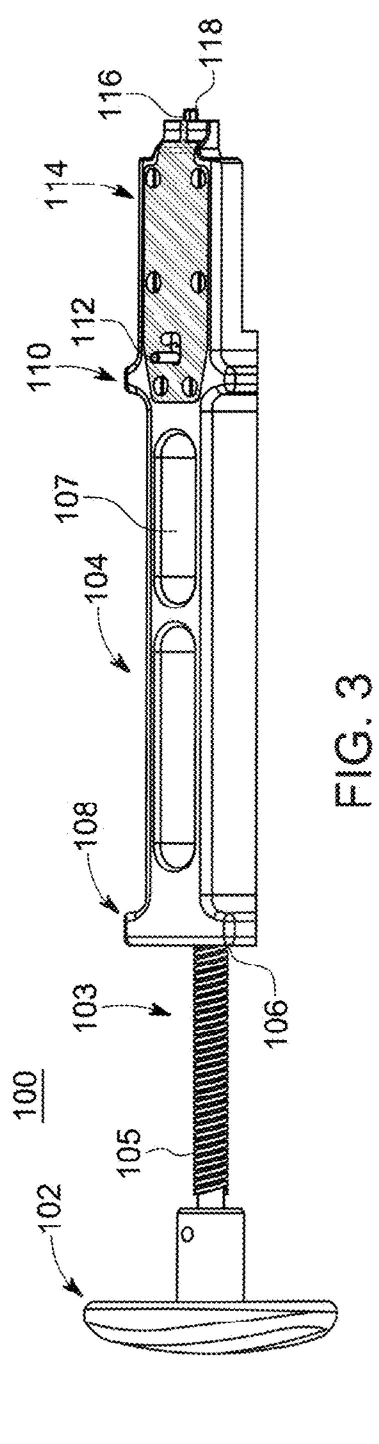
FIG. 3 is another side perspective view of an alternate embodiment of an exemplary instrument for facilitating the implantation of an implant system, in accordance with the present disclosure.

As shown in FIGS. 1-6, the inserter 100 includes a handle portion 102, a body portion 104, and a head portion 110. The handle 102 is shown to be coupled with a rod 105. with the rod 103 extending into a first portion 108 of the body portion 104. The handle 102 includes a gripping portion 109 configured to extend outward from the handle 102. In some aspects, the gripping portion 109 may be configured to interface with one or more instruments in performing at least a portion of a total ankle replacement procedure. The gripping portion 109 may also be configured to be grasped and/or manipulated by a physician in performing at least a portion of a total ankle replacement procedure. As shown, the gripping portion 109 includes a plurality of protrusions that are offset approximately 90 degrees offset from one another. In alternate aspects the gripping portion 109 may include greater or fewer than the four protrusions shown, with said protrusions arranged variously about the handle 102 (e.g., the gripping portion 109 may be spaced equally from one another or may be spaced unequally from one another). In some aspects, the handle 102 may include additional and/or alternate geometries from that shown in FIG. 1. For example, the handle 102 may include a continuous projection extending around the entirety of the handle 102 with an aperture disposed in a central portion of the handle 102 (for example, as shown in FIG. 3). In some aspects the inserter may include multiple handles that may be releasably couplable with the rod 105 so as to provide different gripping portions 109 for interfacing with physicians and/or other instrumentation. Alternate aspects of the inserter 100 may include the handle 102 and gripping portion 109 thereof being integral with the rod 105.

The handle 102 is shown to be coupled with the rod 103, with the rod 103 further being coupled with the body portion 104 of the inserter 100. The rod 103 is received by an opening 106 at a first end 108 of the body portion 104, where the opening 106 has a geometry that is complimentary to that of the rod 103. For example, the rod 103 shown has a substantially cylindrical geometry and the opening 106 is substantially circular/cylindrical. The rod 103 includes a threading 105 disposed along the length of the rod 103, with said threading 105 configured to interface with one or more components of the body portion 104. In some aspects, the opening 106 may include a threading on an interior portion thereof that is complimentary the threading 105 and thus received the threading 105 of the rod 103 such that the rod 103 is translatable along a central axis of the opening 106. In some aspects, the threading 105 may be received by alternate components of the body portion 104. For example, the head portion 110 of the body portion 104 may include complimentary threading configured to receive at least a portion of the threading 105 of the rod 103. In some aspects, manipulation (e.g., twisting/rotating a threaded rod 103, pushing a plunger, etc.) of the handle 102 by a user (e.g., physician) causes translation of the rod 103 as the threading 105 interfaces with one or more complimentary geometries (e.g., opposite threading of opening 106, for example) and may further actuate one or more components of the inserter 100, for example components of the head portion 110. Further, manipulation of the handle 102 (e.g., rotation, thus translating the rod 103) may translate one or more components of an implant 200 used in a total ankle replacement procedure. For example, rotating the handle 102 of the inserter 100 may translate one or more components of the implant 200 toward or away from the body portion 104 of the inserter 100 such that components may be placed, positioned, repositioned, coupled, or otherwise manipulated. In some aspects, the rod 103 may be translatable between one or more predefined positions, with said positions disposed between the handle 102 and the head portion 110 (e.g., various points along the body 104 of the inserter 100). Further, said predefined positions may include locking elements such that the rod 103 may be retained in one or the one or more predefined positions.

The body portion 104 includes a central portion 107 disposed between the first end 108 and the head portion 110.

The central portion 107 may include one or more apertures as shown in FIG. 1 along a length thereof. In some aspects, the apertures of the central portion 107 may be configured such that a user may view the rod 103 as the rod 103 is translated through the body portion 104, with said translation driven by rotation of the handle 102 causing the threading 105 of the rod 103 to interface with one or more components of the body portion 104 (e.g., complimentary threading of the opening 106 and/or the head portion 110, etc.). In some aspects, the central portion 107 may include apertures arranged on one or more sides of the body portion 104, but may also include one or more sides without apertures. For example, in one aspect the central portion 107 may include one or more apertures disposed on only the lateral sides of the body portion 104 of the inserter 100. Conversely, in an additional aspect the central portion 107 may include one or more apertures disposed on only the top and/or bottom surfaces of the body portion 104 of the inserter (for example, as shown in FIG. 3. In some aspects, the central portion 107 may include one or more lateral projections therefrom (for example, adjacent the opening 106) configured to accommodate a user and/or instrumentation implemented in conjunction with the inserter 100.

The head portion 110 of the inserter is configured (e.g., has a geometry that is complimentary/arranged to accommodate interfacing) to interface with one or more components of the implant 200 (see FIGS. 4-6) used in a total ankle replacement procedure. Additionally, the head portion 110 is shown to include a locking mechanism 112 disposed on a top surface thereof, with said locking mechanism 112 translatable by a user between locked and unlocked positions. In some aspects such as that shown in at least FIGS. 1-2, the locking mechanism 112 may be translated within a slot 113 between locked and unlocked positions. For example, the locking mechanism 112 can be in an unlocked position when the locking mechanism 112 is positioned at an end of the slot 113 closest the central portion 107 of the body and can be in a locked position when the locking mechanism 112 is positioned at the end of the slot 113 furthest the central portion 107. In translating the locking mechanism 112 from the locked position to the unlocked position (and vice-versa), a user may prepare the instrument 100 to releasably couple and decouple one or more components of the implant 200.

When the locking mechanism 112 is in an unlocked position, such as that shown in FIG. 2, the locking mechanism 112 may be compressed to release, (e.g., decouple, detach from) one or more other components of a total ankle replacement system. As shown in the exemplary embodiment of FIGS. 1-2, the top surface of the head portion 110 may include instructions 111. The instructions 111 may provide text and/or directional indicators identifying locking and unlocking positions/directions, as well as instructions for compression of the locking mechanism 112 to couple/decouple with the implant 200 and/or components thereof. Such coupling and decoupling of components of the implant 200 enables a user to place, position, and reposition said components of the implant 200 within a joint or adjacent one or more joint surfaces in performing a total ankle replacement procedure. In alternate embodiments, the locking mechanism 112 may include other locking mechanisms in addition to or in place of the slidable locking mechanism 112 as shown in FIGS. 1-2. For example, as shown in FIG. 3, the locking mechanism 112 may include a bolt action latching feature configured such that a portion of the locking mechanism 112 may be manipulated by a user such that translation of the rod 103 (and subsequent movement of any other components such as those of the implant 200) is physically impeded by the combination of the locking mechanism 112 and the head portion 110.

Figures 4, 5:
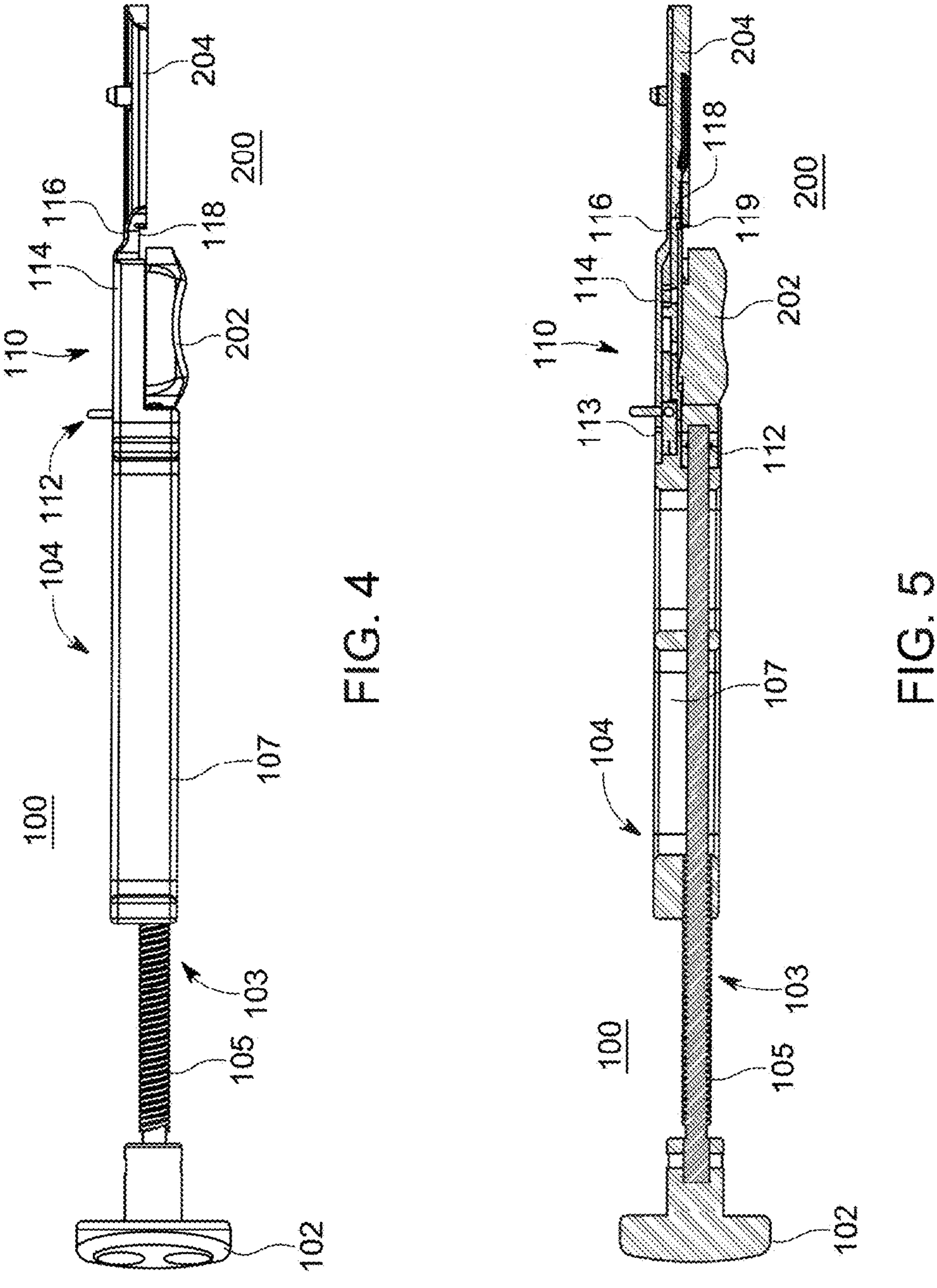
FIG. 4 is another side view of the exemplary instrument of FIG. 1 for facilitating the implantation of an implant system, in accordance with the present disclosure.
FIG. 5 is a side cross-sectional view of the exemplary instrument of FIG. 1 for facilitating the implantation of an implant system, in accordance with the present disclosure.

The head portion 110 is shown to include a protrusion 114 extending from an upper portion of the head portion 110, with said protrusion 114 extending in a direction substantially opposite the handle 102. The protrusion 114 is configured to have a geometry that is complimentary to one or more components of the implant 200 such that said components of the implant 200 may releasably couple with the protrusion 114 of the instrument 100. As shown in FIGS. 4-5, the protrusion 114 includes a projection 116 extending therefrom in a direction substantially opposite the handle 102 (e.g., the projection 116 extends from the protrusion 114 in substantially the same direction that the projection 114 extends from the head portion 110). The projection 116 includes a catch 118 disposed on an end opposite the protrusion 114, with said catch defining a recess 119 configured to facilitate coupling with and positioning/repositioning of the implant 200 and components thereof.

Figure 6:
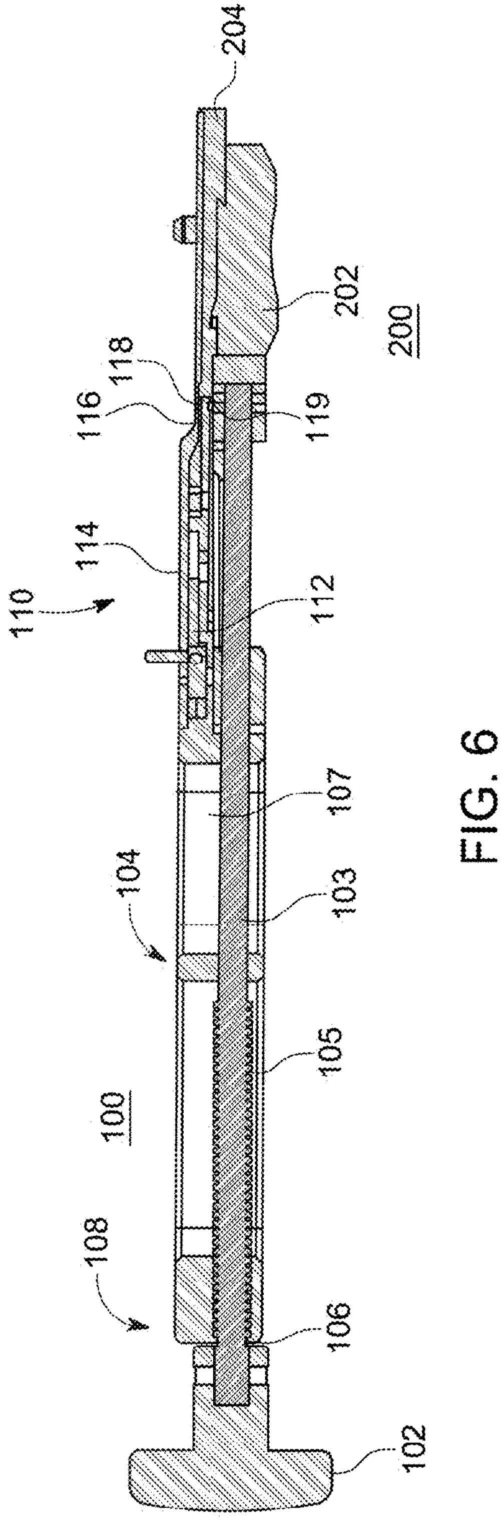
FIG. 6 is another side cross-sectional view of the exemplary instrument of FIG. 1 for facilitating the implantation of an implant system, in accordance with the present disclosure.

Referring to FIGS. 4-6, an insert 202 (e.g., a component of the implant 200) is shown to be positioned adjacent the bottom surface of the protrusion 114. In some aspects, the insert 202 may be releasably coupled or otherwise interface with the protrusion 114. For example, the insert 202 may contact one or more surfaces of the head portion 110 and/or the protrusion 114 thereof so as to prevent movement of the insert 102 in at least the general direction of the handle 102. In some aspects, the insert 202 may be positioned adjacent a joint surface or another portion of the implant 200 (e.g., a talar component) on an inferior side of the insert 202 while interfacing with the bottom surface of the protrusion 114 on the superior side.

Figure 7:
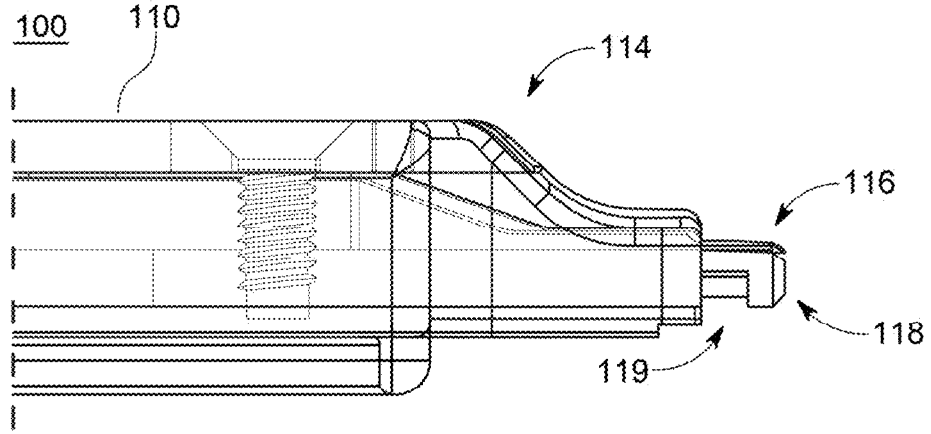
FIG. 7 is a side cross-sectional view of an end portion of the exemplary instrument of FIG. 1 for facilitating the implantation of an implant system, in accordance with the present disclosure.

The projection 116, which includes the catch 118 and recess 119 thereof is configured to couple with a tibial tray 204, as shown in FIGS. 4-6. The tibial tray 206 is configured to couple with the head portion 110 (and projection 116) via the catch 118 and the recess 119. As shown in FIG. 7, the catch 118 and the recess 119 defined by the catch 118 are configured to releasably couple with a complimentary geometry of the tibial tray 204. For example, the catch 118 may interface with and be received by a complimentary recess disposed on the tibial tray 204, while the tibial tray 204 may include a catch configured to simultaneously interface with and be received by the recess 119 defined by the catch 118. As further shown in FIG. 7, the projection 116 (which includes the catch 118 and the recess 119) includes a negative angle so as to prevent movement of the tibial tray 204 as it is inserted into the implant. The negative angle of the projection 116 is configured on a top surface of the projection 116 and may be even with the horizontal (e.g., parallel with the horizontal) or extend forming an angle below the horizontal (e.g., a negative angle). The negative angle formed by the projection 116 thus also forms an angle of 90 degrees or greater with the adjacent portion of the protrusion 114. In some aspects, the projection 116 may include a negative angle of up to 90 degrees below the horizontal so as to immobilized and retain various different aspects of the tibial tray 204 and/or other components of the implant 200.

As shown in FIGS. 4-5, the tibial tray 204 may be coupled with the inserter 100 (via the projection 116, catch 118, recess 119) while the insert 202 is simultaneously positioned beneath the bottom surface of the head portion 110 (e.g., the superior surface of the insert 204 is adjacent at least a portion of the inferior surface of the head portion 110). A user may actuate the handle 102 (e.g., twist, rotate, push toward, the body portion 104, etc.) such that the rod 103 is translated through the central portion of the body portion 104 and toward the head portion 110. Translation of the rod 103 through the body portion 104 may contact or otherwise cause translation of the insert 202 in a general direction opposite the opening 106 of the body portion 104 such that at least a portion of the insert 202 is positioned adjacent and/or directly inferior relative to at least a portion of the tibial tray 204. As the insert 202 is translated, the insert 202 is moved from an anterior to posterior direction with respect to the tibial tray 204 (e.g., the tibial tray 204 is coupled with the projection 116, the catch 118 and the recess 119 at an anterior portion of the tibial tray 204). Accordingly, the insert 202 is disposed below (e.g., inferior) the anterior portion of the tibial tray 204 prior to being disposed below the posterior portion of the tibial tray 204 as the insert 202 is translated by the rod 103. In some aspects, the superior surface of the insert 202 may contact and engage the inferior surface of the tibial tray 204. The insert 202 and/or the tibial tray 204 may include one or more components (e.g., complimentary geometries, engagement features, etc.) to facilitate interfacing of the two components. For example, the tibial tray 204 may include one or more groove configured to receive, accommodate, and retain one or more elongated grooves of the insert 202 (or vice-versa).

As the insert 202 is translated, the tibial tray 204 is configured to remain releasably coupled with the inserter 100. The projection 116, the catch 118, and the recess 119 are configured to interface and couple with the tibial tray 204 such that the tibial tray 204 is retained in a set position while the insert 202 is translated by actuation of the handle 102 (driving the rod 103). For example, the superior surface of the insert 202 may contact the tibial tray 204 as the insert 202 is translated in a direction substantially opposite the opening 106. Such contact of the insert 202 with the insert 204 may apply a force to the insert 204 in a direction substantially the same as or similar to as the translation of the insert 202 (e.g., opposite the opening 106). The tibial tray 204, however, is retained by the projection 116, the catch 118, and the recess 119 such that the insert 202 may be positioned as desired relative to the tibial tray 204. In some aspects the tibial tray 204 and the insert 202 may include complimentary geometries configured to interface and facilitate releasable coupling. Accordingly, the tibial tray 204 is retained by the projection 116, the catch 118, and the recess 119 such that said geometries and/or other coupling features may interface and the insert 202 may be positioned as desired relative to the tibial tray 204, as the tibial tray 204 remains in a set position.

With reference to FIG. 6, the translation of the rod 103 via actuation of the handle 102 may be defined to a specific range of motion. For example, the rod 103 may be configured to have a length such that the contacting of the handle 102 with the body portion 104 (adjacent the opening 106) corresponds to a desired positioning of the insert 202 directly beneath the tibial tray 204. Further, the tibial tray 204 and/or the insert 202 may include features that accommodate a releasable coupling between the two components, with said coupling including one or more geometries/components configured to prevent further translation of the rod 103. Once the insert 202 has been positioned directly superior to the tibial tray 204 as shown in FIG. 6, the two components may be inserted into a prepared joint space using the inserter 100. In some aspects, the tibial tray 204 and the inserter 202 may be manipulated to interface/couple with other components of the implant 200 and/or the joint of the patient in performing a total ankle replacement procedure. In some aspects, the tibial tray 204 and/or the insert 202 may be decoupled from the inserter 100 prior to implantation in a patient or coupling with other devices/instruments implemented in a total ankle replacement procedure. In some aspects, the tibial tray 204 may be positioned adjacent a prepared tibial surface using the inserter 100, with the tibial tray 204 and/or the insert 202 simultaneously decoupled from the inserter when the desired position within the joint space has been achieved.

In releasing the tibial tray 204 and/or the insert 202 from the inserter 100, a user/physician may reference the instructions 111 provided on one or more surfaces of the inserter. As shown in FIG. 1, the instructions 111 are disposed on a superior surface of the head portion 110 adjacent the locking mechanism 112. Further to the aspect shown in FIG. 1, the instructions 111 may indicate that the tibial tray 204 (which may be coupled with the insert 202) may be released from the inserter 100 by applying downward pressure to the locking mechanism 112. Thus, when the desired placement of the tibial tray 204 and insert 202 has been achieved, a physician may release (e.g., decouple) the tibial tray 204 and/or the insert 202 from the instrument by pressing down on the locking mechanism 112. Once released, the handle 102 and rod 103 may be returned to the position as shown in FIG. 1 by actuating the handle in a manner opposite that used to actuate the insert 202 previously (e.g., rotation in opposite direction, retracting plunger in direction opposite that was pushed, etc.).

Figures 8, 9:
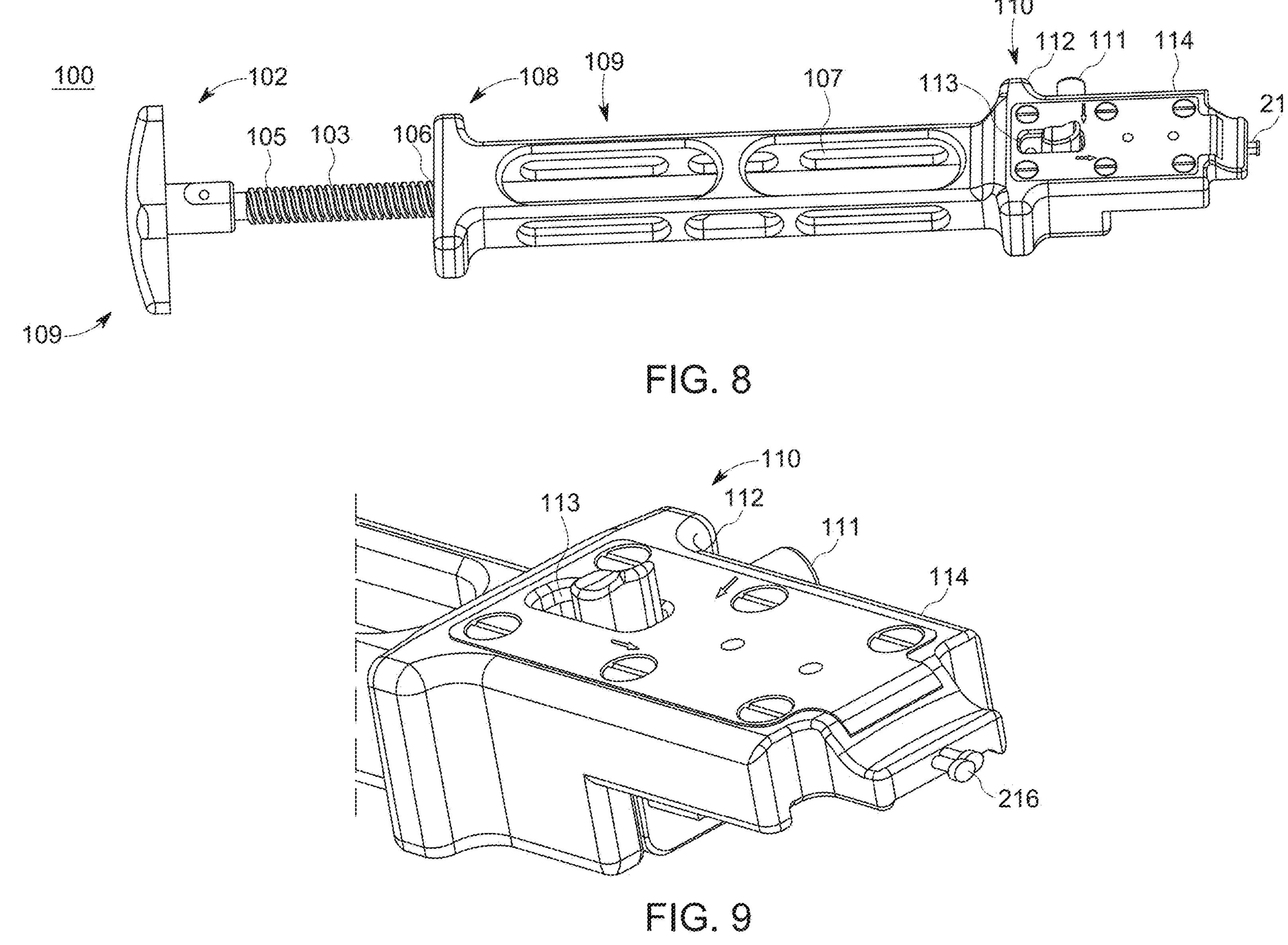
FIG. 8 is a side elevational perspective view of the exemplary instrument of FIG. 1 for facilitating the implantation of an implant system with alternate components, in accordance with the present disclosure.
FIG. 9 is an enlarged side elevational perspective view of an end portion of the exemplary instrument of FIG. 8 for facilitating the implantation of an implant system, in accordance with the present disclosure.
Figure 10:
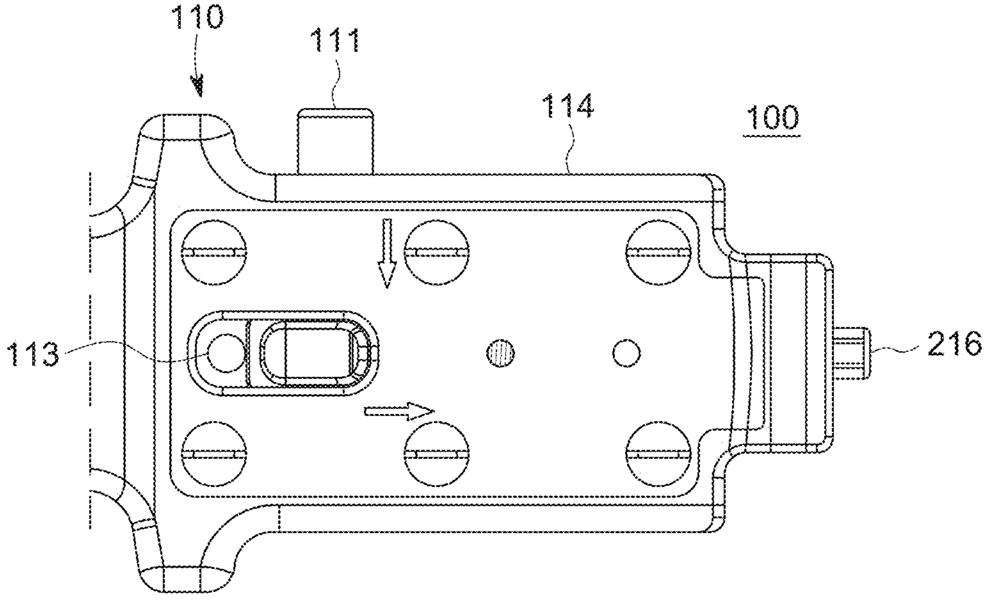
FIG. 10 is an enlarged top view of an end portion of the exemplary instrument of FIG. 8 for facilitating the implantation of an implant system, in accordance with the present disclosure.
Figure 11:
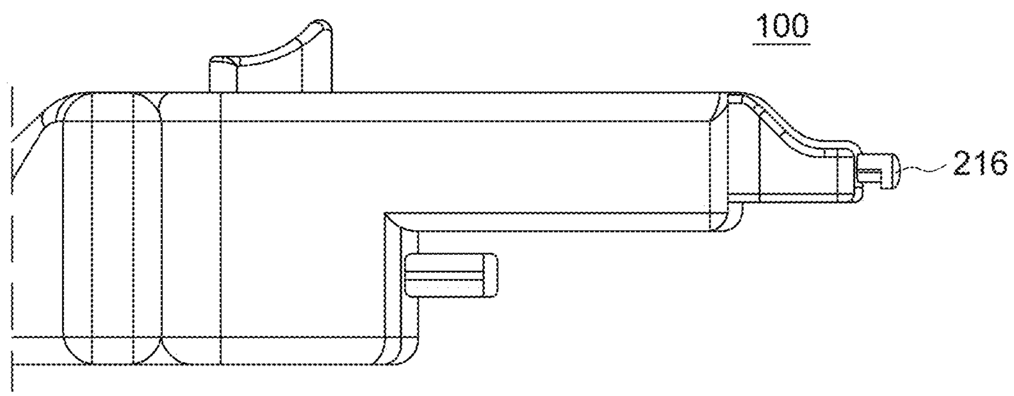
FIG. 11 is an enlarged side view of an end portion of the exemplary instrument of FIG. 8 for facilitating the implantation of an implant system, in accordance with the present disclosure.
Figure 12:
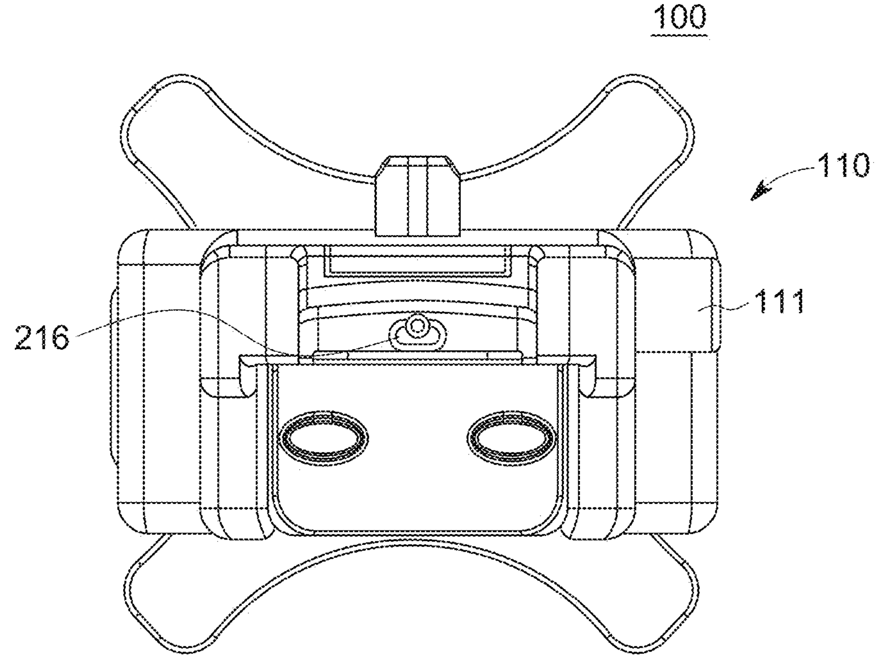
FIG. 12 is an enlarged front view of an end portion of the exemplary instrument of FIG. 8 for facilitating the implantation of an implant system, in accordance with the present disclosure.

Referring now to FIGS. 8-12, the inserter 100 is shown in a configuration similar to that shown in the embodiments of FIGS. 1-7, but may also include alternate components. In some aspects, the inserter 100 of FIGS. 8-12 may include one or more components that are the same as or similar to the inserter 100 of FIGS. 1-7, for example purposes only, the handle portion 102, the body portion 104, and the head portion 110 (as well as components thereof). The inserter 100 is shown to include a projection 216 disposed on a distal portion of the head portion 110 and extending distally from the head portion 110. As shown, the projection 216 is positioned in the same and/or a similar position to the projection 116 as shown and described previously herein. The projection 216 may include a pin or other resilient member positioned adjacent (or, as shown in FIG. 9, for example, superior/dorsal) a rigid member that may be the same as and/or similar to the projection 116. The projection 216 is configured to releasably couple with a tibial tray of an ankle arthroplasty system, for example the tibial tray 204 of the implant 200 as shown and described previously (though the projection 216 may also facilitate releasable coupling with one or more other components of one or more ankle arthroplasty systems). For example, the tibial tray 204 may include a depression (e.g., a bore, a recess, an aperture, etc.) configured to receive at least a portion of the projection 216 (which may include the resilient member and/or the rigid member) such that the projection 216 may releasably couple with the tibial tray 204.

The inserter 100 may also include a locking mechanism the same as and/or similar to the locking mechanism 112 (e.g., retention mechanism, actuatable releasable coupling mechanism, etc.) as shown and described previously so as to retain the tibia tray 204 when releasably coupled with the projection 216. For example, the locking mechanism 112 may include one or more actuators (e.g., buttons, etc.) that actuate one or more components of the inserter 100. The locking mechanism 112 may, for example, manipulate the resilient member of the projection 216 relative to the rigid member so as to facilitate the releasable coupling and/or decoupling of the tibial tray 204. When implanting the implant 200, a physician may releasably couple the tibial tray 204 with the inserter 100 via the projection 216 (and may also releasably couple other implant components to the inserter 100, simultaneously or otherwise), position the tibial tray 204 as desired, and actuate the locking mechanism 112 so as to release the tibial tray 204 from the projection 216, thus placing the tibial tray 204 in a desired position. Manipulation of the locking mechanism 112 may depress, extend, withdraw, or otherwise actuate at least a portion of the projection 216 (e.g., the resilient member relative to the rigid member) so as to initiate releasable coupling and/or initiate decoupling of the tibial tray 204 from the inserter 100. In positioning the tibial tray 204 as desired, the physician may manipulate one or more other portions of the inserter 100, for example, the gripping portion 109 so as to actuate at least a portion of the rod 105 and/or 103, thus translating the tibial tray 204 along a longitudinal axis of the inserter 100.

It should be noted that the components, features, and other aspects of the inserter 100 as shown in one or more of FIGS. 1-12 may be interchangeable between one or more of the embodiments shown and described herein. That is to say that, for example, the inserter 100 as shown in FIG. 1 may be modified so at to include one or more of the features and/or components as shown and described in FIGS. 8-12. Furthermore, the inserter 100 as shown and described herein may be modified to accommodate one or more components of an implant system which may include, for example, the total ankle arthroplasty systems incorporated by reference herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. A system, comprising;

an implant system, comprising:

a tibial component;

a talar component;

an intermediate component; and an instrument comprising:

a handle portion coupled to a rod;

a head portion comprising a releasable coupling portion configured to releasably couple with the tibial component, wherein the head portion is configured to releasably couple with the intermediate component, and wherein the coupling portion comprises a protrusion extending from an upper portion of the coupling portion, wherein the protrusion comprises:

a projection for engaging at least a portion of the tibial component, wherein the projection comprises:

a catch disposed on an end of the projection; and a notch defined by the catch to couple with the tibial component;

an engagement feature on a bottom surface of the protrusion, wherein the engagement feature slidingly couples with the intermediate component, and wherein the rod contacts with the intermediate component to translate the intermediate component relative to the coupling portion; and a body portion, wherein the body portion is disposed between the handle portion and the head portion.

2. The system of claim 1, wherein the tibial component and the intermediate component are simultaneously releasably couplable with the head portion of the instrument such that the tibial component is positioned superior relative to the intermediate component.

3. The system of claim 1, wherein the handle portion of the instrument further comprises a gripping portion, wherein the rod is threaded, and wherein the threaded rod extends at least partially into and through the body portion of the instrument.

4. The system of claim 3, wherein the body portion of the instrument comprises a complimentary threading that receives at least a portion of the threaded rod.

5. The system of claim 4, wherein manipulation of the gripping portion actuates the threaded rod along a longitudinal axis of the instrument.

6. The system of claim 5, wherein actuation of the threaded rod along the longitudinal axis repositions the intermediate component relative to the tibial component in a proximal-distal direction.

7. An instrument comprising:

a handle coupled with a rod;

a body portion comprising a first end and a head portion, the body portion configured to receive the rod in a central portion thereof; and a coupling portion configured to releasably couple with one or more components of an implant system, wherein the coupling portion comprises a protrusion extending from an upper portion of the coupling portion, wherein the protrusion comprises:

a projection configured to engage at least a portion of a first component of the one or more components of the implant system, wherein the projection comprises:

a catch disposed on an end of the projection; and a notch defined by the catch and configured to couple with the first component of the one or more components of the implant system;

an engagement feature on a bottom surface of the protrusion, wherein the engagement feature is configured to slidingly couple with a second component of the one or more components of the implant system, and wherein the rod is configured to contact the second component to translate the second component relative to the coupling portion.

8. The instrument of claim 7, wherein actuation of the handle moves the rod to actuate a second implant component relative to a first implant component so as to position the second implant component adjacent the first implant component.

9. The instrument of claim 8, wherein the second implant component is an insert for a total ankle replacement implant.

10. The instrument of claim 8, wherein the first implant component is a tibial tray for a total ankle replacement implant.

11. The instrument of claim 8, wherein the second implant component is releasably couplable with the first implant component.

12. The instrument of claim 8, wherein the coupling portion is configured to releasably couple with the first implant component such that the first implant component remains in a fixed position while the second implant component is actuated.

13. The instrument of claim 12, wherein the first implant component comprises a complimentary geometry to the catch and the notch such that the catch is received by a portion of the first implant component.

14. The instrument of claim 7, wherein the coupling portion comprises an actuator configured to facilitate engagement with and release of at least one of the one or more components of the implant system.

15. The instrument of claim 7, wherein the rod comprises a first threading disposed along a length of the rod.

16. The instrument of claim 15, further comprising a second threading disposed in the body portion, wherein the second threading is complimentary to and receives the first threading and an actuation of the handle causes translation of the rod through the body via the first and second threading.

17. A method for positioning implant components, comprising:

selecting a desired size of a first implant component and a corresponding size of a second implant component;

releasably coupling the first implant component and the second implant component with a distal end of an insertion instrument, wherein the first implant component is arranged superior relative to the second implant component, wherein the insertion instrument comprises:

a handle coupled with a rod;

a body portion comprising a first end and a head portion, the body portion configured to receive the rod in a central portion thereof; and a coupling portion configured to releasably couple with one or more of the first implant component and the second implant component, wherein the coupling portion comprises a protrusion extending from an upper portion of the coupling portion, wherein the protrusion comprises:

a projection configured to engage at least a portion of the first implant component, wherein the projection comprises:

a catch disposed on an end of the projection; and a notch defined by the catch and configured to couple with the first implant component;

an engagement feature on a bottom surface of the protrusion, wherein the engagement feature slidingly couples with the second implant component, and wherein the rod contacts the second implant component to translate the second implant component relative to the coupling portion;

selectively repositioning the second implant component relative to the first implant component;

positioning the first and second implant components relative to a tibia of a patient; and decoupling the first and second implant components from the insertion instrument.

* * * * *